United States Patent [19]

Walton

[11] Patent Number: 4,586,288
[45] Date of Patent: May 6, 1986

[54] TISSUE CULTURE ROOTING SYSTEM

[75] Inventor: Charles F. Walton, Hudson, Ohio

[73] Assignee: Smithers-Oasis Company, Kent, Ohio

[21] Appl. No.: 514,564

[22] Filed: Jul. 18, 1983

[51] Int. Cl.⁴ .............................................. A01G 9/02
[52] U.S. Cl. ........................................... 47/73; 47/87
[58] Field of Search ................ 47/DIG. 7, 64, 86, 60, 47/62, 63, 65, 9, 14, 87, 74, 73

[56] References Cited

U.S. PATENT DOCUMENTS

| 3,524,279 | 8/1970 | Adams | 47/64 X |
| 3,755,964 | 9/1973 | Rack | 47/74 |
| 3,961,444 | 6/1976 | Skaife | 47/79 |
| 3,973,355 | 8/1976 | McKenzie | 47/86 X |
| 4,224,765 | 9/1980 | Song | 47/66 X |
| 4,241,537 | 12/1980 | Wood | 47/DIG. 7 X |

FOREIGN PATENT DOCUMENTS 7800680  7/1979  Netherlands ............................ 47/86

OTHER PUBLICATIONS

*Modern Potting Composts*, A. C. Bunt 1976, pp. 40, 41, "Alternative Materials".

*Primary Examiner*—Robert A. Hafer
*Assistant Examiner*—Danton DeMille
*Attorney, Agent, or Firm*—Renner, Kenner, Greive, Bobak & Taylor

[57] ABSTRACT

A novel tissue culture assembly (10) which employs a tray (11) that presents one or more cavities (12) opening upwardly through a web sheet (13). A unique growing medium (25) is received in each cavity (12) and comprises a mixture of granulated foam (26) and pulverized gel (28). A membrane (35) spans the opening of each cavity and is secured to the tray (11). An aperture (36) pierces the membrane (35) at approximately the central portion of the cavity opening, or mouth (17), and the sides (38) of the aperture (35) engage a propagule (40) inserted through the aperture to support the propagule. The base (19) of each cavity (12) is provided with an aperture (20) by which selected fluids may gain ingress and egress with respect to the cavity. A domed cover (60) may be removably secured to the tray (11).

8 Claims, 7 Drawing Figures

TISSUE CULTURE ROOTING SYSTEM

FIELD OF THE INVENTION

The present invention relates generally to the aseptic culture of plant cells, tissues and/or organs in a vessel containing a nutrient and hormone bearing, germ free, growing medium under controlled, environmental conditions suitable for plant morphogenesis.

BACKGROUND ART

The possibility of plant cell, tissue and/or organ culture—more commonly, and generically, referred to as plant tissue culture—was surmised as early as 1902 by G. Haberlandt. Although unsuccessful, he reasoned that hormonal regulation of cell division, growth and differentiation would be the key to successful organogenesis. Approximately a half century later, in 1956, Messrs. Skoog and Miller established that organogenesis was, in fact, regulated by quantitative interactions between growth factors, especially auxins and cytokinin in the culture medium. High auxin levels induce root initiation and repress shoot formation, whereas high cytokinin levels have the opposite effect. Once it was appreciated that an auxin and cytokinin balance is a general phenomenon critical to organogenesis, tissue culture technology became a commercial propagation tool rather than a mere academic exercise.

The two principle advantages of using tissue culture technology are that: (1) it permits rapid clonal propagation of plants with selected attributes and in large quantities; and (2) it permits recovery and propagation of specific pathogen-free plants i.e., plants free of specifically known and detectable fungi, bacteria, viruses, and viroids.

From a highly practical point of view tissue culture greatly reduces the vast greenhouse space heretofore required to house the parental stock inasmuch as microcuttings and plantlets are now readily available, year round, from parental stock cultures in micropropagation laboratories. Moreover, tissue culture production can be initiated at any time the appropriate plant explants are available, i.e., actively growing shoot tips, runner tips, etc.

Although specific procedures may well vary, most tissue culturists employ the same basic steps. Preparatory to the four stages of the actual tissue culture process, of course, one must first determine which part of the plant will be used. Because various plants may react differently, the specific part of the plant that can be most successfully employed for propagation by virtue of the tissue culture technology must be determined. For example, with ferns the runner tip is preferred, but other plants may culture more effectively from lateral buds, shoot tips, leaf parts or even sections of pollen, seeds or fruit. If a specific plant has been researched, the explant and cultural information will generally be available; otherwise, the lab propagator must develop that information on his own or have it developed through a research laboratory. Once determined, the appropriate plant parts, or "explants", are removed, their surfaces are disinfected, and they are inserted, according to the most rigorous aseptic techniques, into a previously prepared starter medium in a culture vessel. The vessel is then capped, or otherwise closed, to minimize contamination from the external environment.

Before continuing with a general background explanation of the heretofore employed tissue culture techniques, it should be appreciated that one must select a starter medium appropriate to the particular plant that is to be propagated. One exemplary starter medium that can be employed with a wide variety of plants is an inorganic salt mixture such as the well known Murashige and Skoog mixture which contains organic chemicals with the proper auxin/cytokinin balance for the particular plant being propagated by the tissue culture technique.

Such a mixture contains a variety of salts—viz., nitrates, sulfates, halides, potassium, boron and molybdenum—as well as iron, ethylene diamine tetraacetic acid, vitamins, sugar and the auxin/cytokinin balance. This mixture is added to distilled water and, though not necessarily, agar (a jelly-like substance made from seaweed) and brought to the desired pH by the addition of sodium hydroxide and/or hydrochloric acid. Thereafter, the mixture, if it contains agar, is heated and agitated until the agar is melted. While still hot the mixture is dispensed into tubes, or other culture vessels, which are then closed, as by stoppers, foil or suitable plastic wrap, and sterilized.

After the sterilized, starter medium cools it is ready for "Stage I" which is initiated by the aforedescribed insertion of the explants into the starter medium contained within the culture vessels. Throughout Stage I the closed vessels are maintained in an environment of controlled photoperiod, light intensity and temperature for a period of time appropriate to the particular plant. After about six weeks (the average time) the explant will have enlarged and may have formed a cluster of cells (termed a "callus"), and axillary shoots or adventitious shoots may be evident.

Stage II begins when those explants which are visibly free of contamination and which have established themselves in the starting medium of Stage I are subdivided and cultured in a multiplication, or nutrient, medium (this medium differs from the starter medium by employing a higher cytokinin to auxin ratio). At this stage the weaker explants, or propagules, and the unwanted "sports" can be eliminated. The subdivision and culturing process of Stage II can usually be repeated up to three or four times, but after that epigenetic changes can become an increasing problem with some plant types. During Stage II the propagules are not only very delicate but are also heterotrophic and receive all their nourishment from the medium itself; there is little or no photosynthesis occuring to provide food. Moreover, the propagules must be maintained in a sterile environment inasmuch as the sugar in the multiplication, or nutrient, medium provides a growth medium for unwanted micro-organisms, as well.

At the time of their last reculture and division the propagules enter Stage III. In Stage III the propagules are of sufficient number and of such size that they are ready for rooting and transfer to a pre-transplant, or hardening medium (this medium differs from the multiplication, or nutrient, medium, by employing a higher auxin to cytokinin ratio). This stage involves rooting the propagule in vitro, initiating the change from the heterotrophic stage (in which the cultured tissue derives nourishment solely from that added to the culture medium) to the autotrophic state (self nourishing by virtue of photosynthesis) and aclimating the resulting plantlet to be capable of survival in vivo.

After several weeks in Stage III the plantlets must be established in an in vivo medium, such as soil or a soil-like medium; this constitutes Stage IV. The transition which must be accomplished during Stage IV is perhaps the most drastic environmental change experienced during the tissue culture process. Specifically, the plantlet is subjected to lower humidity, higher light levels and for the first time it has been transplanted from an in vitro culture to an in vivo soil-like medium.

If the conditions are not carefully controlled, the plantlets may die, or exhibit reduced subsequent development. The soil-like medium must be prepared to be free of pathogens while providing sufficient soil irrigation and moisture to stimulate rapid root development. Moreover, high humidity, reduced light and moderate to warm temperatures must be initially maintained and gradually changed to the ambient environmental conditions of a greenhouse over several weeks to effect a satisfactory transition.

As should certainly be appreciated, the multiple steps involved in the tissue culture process are highly labor intensive. Not only must the tissues be repeatedly handled, the culture medium must be formulated differently from stage to stage.

The agar based media that is currently rather extensively employed in the tissue culture process requires a heating-cooling cycle in conjunction with the preparation of the culture media. Moreover, a high concentration of sugar is required in the agar medium to provide a nutrient to the heterotrophic propagules during root initiation. This necessitates washing the sugar off the plantlets immediately prior to their being transplanted into the Stage IV environment in order to minimize the likelihood of micro-organism development which would reduce plantlet survival in vivo.

SUMMARY OF INVENTION

It is, therefore, a primary object of the present invention to provide the means whereby to lessen the labor intensity of the tissue culture process.

It is another object of the present invention to obviate the necessity of using agar in at least the latter stages of the tissue culture process.

It is a further object of the present invention to provide a unique soil-like culture medium that can be employed after Stage II of the tissue culture sequence and that is fully compatible with conventional greenhouse growing media and thereby eliminates Stage III per se, and reduces labor and costs associated with that Stage.

It is a still further object of the present invention to provide a growing medium that is naturally plant pathogen-free and need not, therefore, be independently sterilized but which can be readily pasteurized, if exposed to pathogenic micro-organisms.

It is yet another object of the present invention to provide a growing media container which permits the plants to be grown in individual units, employs a common means not only to retain the growing medium within the container but also to position and retain the plant with respect to the growing medium and further permits a convenient means by which to grade the plants and to serve as a non-spill shipping container that assures adequate moisture to the roots during transportion.

It is an even further object of the present invention to provide a growing media container, as above, the configuration of which permits soil sub-irrigation and mist propagation without destroying the air/water balance within the growing media.

These and other objects, as well as the advantages thereof over existing and prior art forms, will be apparent in view of the following detailed description of the attached drawings, and are accomplished by means hereinafter described and claimed.

In general, a tissue culture assembly embodying the concept of the present invention employs a tray which presents one or more cavities that open upwardly through a web sheet. A unique growing medium is received within the cavities, and each cavity is perforated to permit ingress and egress of fluid to the medium. A membrane spans the opening of the cavity and is secured to the web wall surrounding the opening at what is normally the upwardly directed end of the cavity. An aperture pierces the membrane at approximately the central portion of the opening to receive a tissue culture propagule therethrough. The sides of the membrane delineating the aperture engage the propagule to support the same and to maintain said propagule in a predetermined relationship with respect to the medium within said cavity.

One preferred embodiment of the present invention is shown by way of example in the accompanying drawings and described in detail without attempting to show all of the various forms and modifications in which the invention might be embodied; the invention being measured by the appended claims and not by the details of the specification.

DETAILED DESCRIPTION OF A PREFERRED EMBODIMENT

Figure 1:
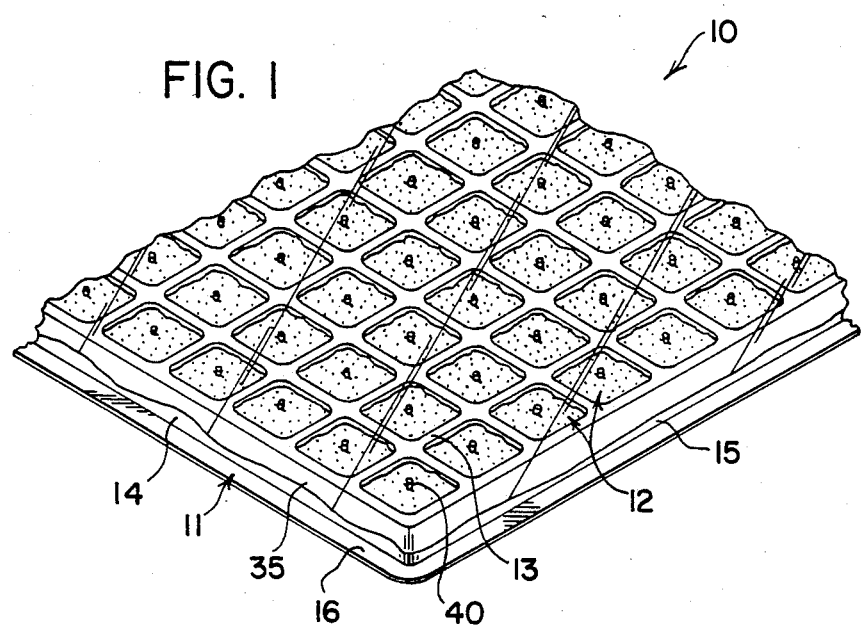
FIG. 1 is an oblique perspective depicting a portion of a tray having a plurality of cavities, each of which contains a unique growing medium, the tray being covered by a membrane that has been pierced to support a propagule.
Figure 2:
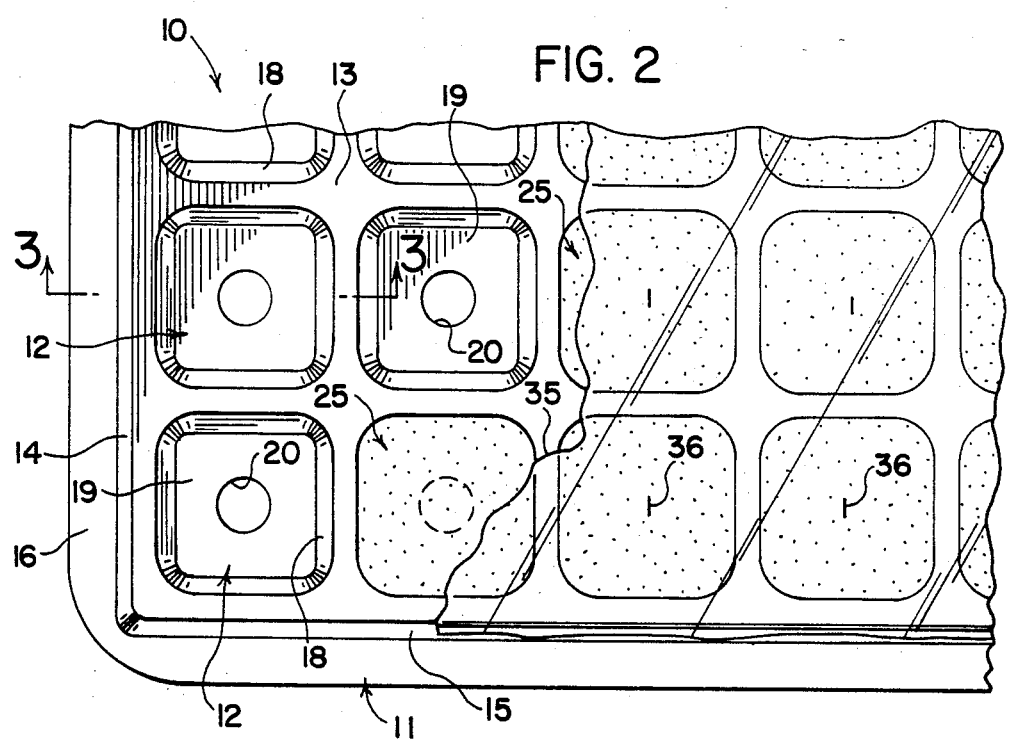
FIG. 2 is an enlarged top plan view of a portion of a tray, such as depicted in FIG. 1, with the membrane partially broken away and wherein certain cavities are represented as containing the medium while others are represented as empty.
Figure 3:
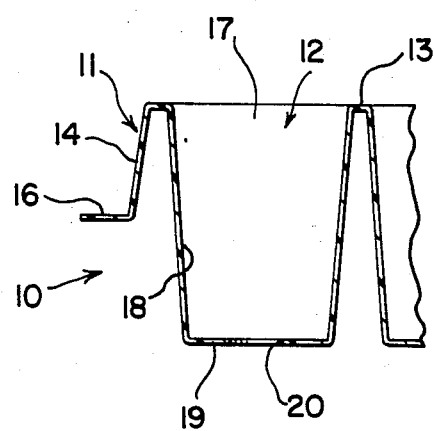
FIG. 3 is a cross sectional view taken substantially along line 3—3 of FIG. 2 and depicting an empty cavity.

A tissue culture assembly is identified generally by the numeral 10 on the attached drawings. The assembly 10 employs a cavity tray 11. Although one may, when armed with an understanding of the present invention, well fashion the configuration of the cavity tray most judiciously to accommodate the specific requirements of a particular plant or even to be dimensionally compatible with a particular commercial installation, a perfectly satisfactory cavity tray for general usage can be prepared by providing a plurality of cavities 12 which are supportingly depended from a planar web sheet 13.

As best depicted in FIG. 1, a plurality of cavities 12 may be aligned in rows and columns to depend from the web sheet 13. The intersecting lateral sides 14 and 15 of the sheet 13 may extend downwardly to terminate in a horizontally oriented, reinforcing flange 16.

Each of the cavities 12 is circumscribed by an inverted, frustro-pyramidal sheath 18, the basal perimeter of which is integrally connected to the web sheet 13 to delineate the mouth 17 of the cavity 12 defined by that sheath, the mouth constituting the opening at what is normally the upwardly directed end thereof. The depth of each cavity is delimited by a base 19 which caps the end of the sheath 18 in spaced relation below the web sheet 13. As shown, each base 19 may be provided with at least one perforation 20 to provide for selective ingress and egress of fluid to and from the individual cavities 12. The size of the perforation 20 should not permit the medium to fall out of the cavity 12, and as such the size of the perforation(s) will have to be selected accordingly. In conformity with accepted practice no scale is intended by the perforation depicted.

Figure 4:
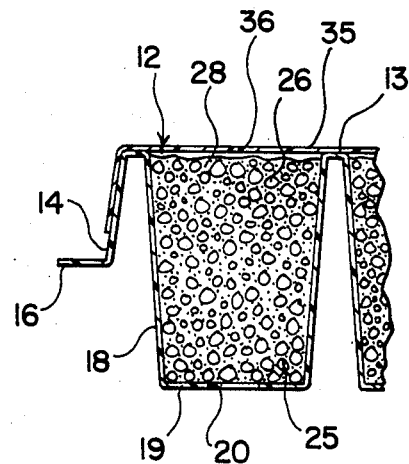
FIG. 4 is a cross sectional view similar to FIG. 3 but depicting the cavity filled with the unique medium and covered by a membrane.

Each cavity 12 is filled with a unique growing medium 25. The growing medium is preferably comprised of a granulated, porous filler 26 (FIG. 4) to which a pulverized, starched gel 28 is added in an amount equal to from 3 to 10 percent of the total medium 25, by weight.

The filler employed is preferably a wettable, open-celled polyurethane foam, but it may also be made from phenol-formaldehyde resin, the latter foam being the type readily available under the universally known trademark OASIS. In short, such foam is made from a liquid, phenolformaldehyde resin to which is added the foaming agent, a surfactant and a catalyst. The proportions of these materials are varied in accordance with the characteristics desired for the resulting foam. Inasmuch as this process is well known, elaboration on the manufacturing techniques is deemed superfluous. Suffice it to say that the desired foam preferably has a density within the range of about 0.75 to approximately 2.5 pounds per cubic foot (0.012 to 0.04 grams/cm$^3$); a pH within the range of about 4.5 to approximately 7.5; and, is granulated to pass through a ¼ inch (cm) screen, which results in a bulk density within the range of about one to approximately five pounds per cubic foot (0.016 to 0.08 grams/cm$^3$).

Although the aforesaid foams have been found to be applicable for use in conjunction with the culture of the vast majority of plant cells, tissues and/or organs, it has also been determined that vermiculite, peat moss or other such materials, if properly sterilized, may also be employed quite effectively as filler material in conjunction with, or independently of, such foams.

The gel 28 which is intermixed with the, aforesaid filler, or granulated foam, may be virtually any hygroscopic gel, but an exemplary gel which works quite well is a copolymer of potassium propenoate-propenamide that has been pulverized to pass a 20 mesh screen (0.0331 inches; 0.0084 cm). The gel is employed in a range of approximately 3-10 percent of the medium, by weight.

A membrane 35 is secured to the web sheet 13 in order to span the mouth, or opening 17 at the upwardly directed end, of each cavity 12. The means by which the membrane is secured is irrelevant; it may be secured by a heat welding operation or may even be secured by the use of an adhesive. In any event, the membrane 35 will serve to maintain the growing medium 25 within each cavity 12 and also serve to constitute a shield by which to prevent the medium 25 from contamination.

The membrane 35 is preferably a thermoplastic material. One such material is a polyvinylidene chloride polymer, or copolymer, which is known generically as "saran". Numerous other plastic materials would be perfectly suitable for achieving the heretofore, and hereinafter, described functions of the membrane.

Figure 5:
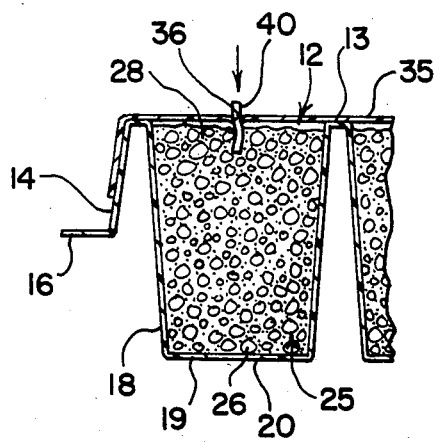
FIG. 5 is a cross sectional view similar to FIG. 4 but with a propagule inserted through, and supported by, the membrane and with a portion of the propagule received within the medium in said cavity.
Figure 6:
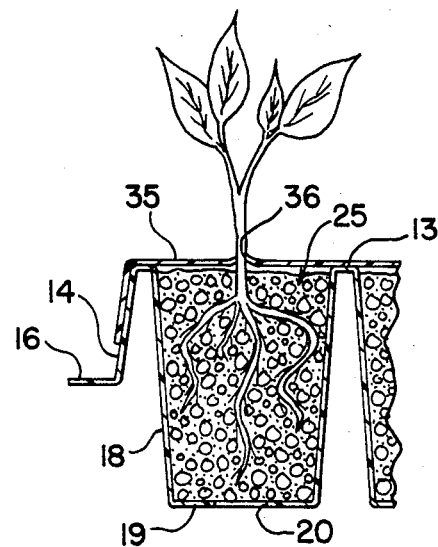
FIG. 6 is a further cross sectional view similar to FIGS. 4 and 5 but with the propagule having become a plantlet; and, FIG. 7 is a still further cross sectional view similar to FIGS. 4, 5 and 6 but depicting the plantlet having become a full fledged plant for shipment in the tray without transplanting having been required.

In order for the propagule 40 to be received in the tissue culture assembly 10, the membrane 35 must be pierced to provide an aperture 36 that is located generally centrally of the mouth 17 of the cavity 12. The medium 25 is pre-wetted, and that portion of the propagule 40 onto which the roots are to be formed is then inserted through the aperture 36 and into the growing medium 25, as depicted in FIG. 5.

The pulverized, hygroscopic gel and granulated foam combine to provide a wet, but well irrigated, environment for root initiation and growth, and the membrane serves not only to anchor the propagule in position during root formation but also improves the relative humidity at the root environment.

Figure 7:
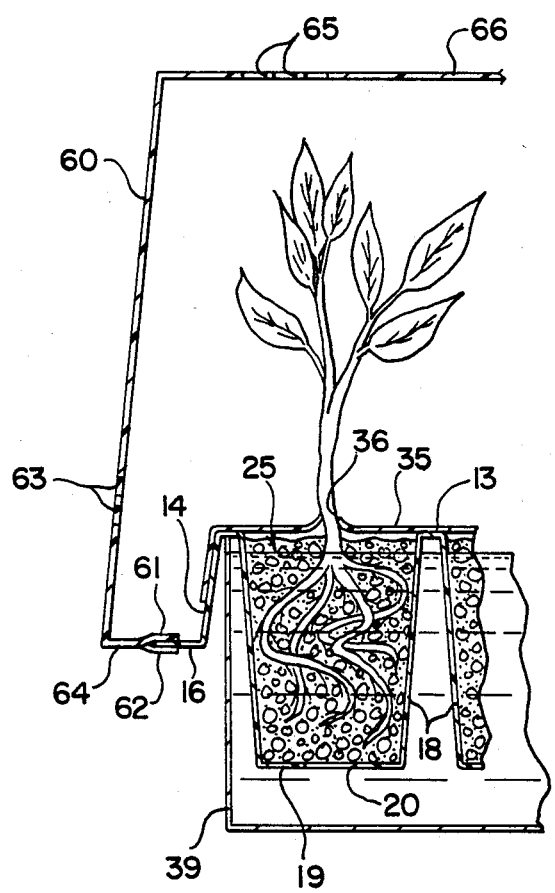
FIG. 7 also depicts a domed cover being supported by the tray, the latter being reposed in a reservoir whereby to flood the cavities either to flush unwanted nutrients and/or hormones or to provide the desired nutrients and/or hormones.

Nutrients and hormones can be readily added to the medium, as required, or desired, and can, conversely, be readily flushed from the medium. In this regard the tray 11 may be reposed in the desired fluid. That is, the tray need not be fully immersed, but merely set into the fluid so that the fluid can flood each cavity 12 by gaining ingress through aperture 20. For the most efficient and effective transfer of fluid one may substantially immerse the cavities within the fluid to such an extent that the surface of the fluid lies just beneath the web sheet 13, as depicted in FIG. 7. Thus, the cavity tray 11 may be reposed in a reservoir 39 of water for a sufficient period of time to permit the water to flood the cavities 12. Thereafter, the tray 11 is removed from the reservoir and a substantial portion of the water in each cavity will drain through aperture 20. Two or more such flushings will effect virtually a complete exchange of the fluid held by the gel as well as the nutrients and/or the hormones therein.

After the cavities 12 have been so purged, the tray 11 may be reposed in a reservoir containing the desired nutrients and/or hormones, and they will be absorbed into the gel and foam for use by the propagule, plantlet and, eventually, the resulting plant.

The granulated foam permits relatively free exchange of fluid and also provides the requisite aeration through the medium so long as the tray is not reposed in a fluid reservoir. The gel, on the otherhand, being hygroscopic retains fluid and serves as the source of fluid for the propagule, plantlet or plant served by the medium.

Thus, it should now be appreciated that by using the unique medium 25, and by varying the nutrient mixture supplied thereto by the fluid in which the tray may be periodically reposed, one may obviate Stage III entirely. Moreover, the propagule, once planted as depicted in FIG. 5, will remain in the same medium 25, and even the same tray 11, as the propagule is transformed into a plantlet. Certainly the nutrients and growth factors (such as the auxin and cytokinin) will be varied, as required, by virtue of the flushing technique, but the medium itself will not be changed.

Finally, because the medium 25 is fully compatible with soil-like media, the resulting plant can be shipped and sold in a tray 11 containing the medium for eventual transplanting into an actual soil-like environment.

To facilitate shipment of the tender plantlets, or young plants, one may secure a domed cover 60 to the reinforcing flange 16. Such a cover 60 could well be provided with a plurality of tabs 61 and 62 to engage the flange 16 and maintain the cover in position. The cover will serve to maintain an elevated humidity level therebeneath; will protect the plants against physical damage; and, may be tinted, as desired, to shield the contents of the tray from direct sunlight. To effect related protection, the dome 60 may also be provided with a plurality of peripheral bores 63 near the base 64 of the dome as well as a plurality of holes 65 along the apex 66 of the dome to permit the circulation of air through the dome should the temperature of the air within the dome rise unacceptably.

It should, therefore, be apparent that the tissue culture assembly hereinbefore described, and including the unique medium, effectively obviates the necessity for further replanting following what is customarily the end of Stage II and otherwise accomplishes the objects of the invention.

I claim:

1. A tissue culture assembly comprising:
   a tray having at least one cavity, each said cavity having a mouth at which is normally the upwardly directed end thereof;
   a growing medium received by said cavity, said medium comprising a porous granulated foam filler mixed with a hygroscopic gel,
      said foam filler having a density in the range of from about 0.75 to approximately 2.5 pounds per cubic foot (0.012 to 0.04 grams/cm$^3$) and granulated to pass a 0.25 inch (0.635 cm) mesh screen resulting in a bulk density range of from about 1 to approximately 5 pounds per cubic foot (0.016 to 0.08 grams/cm$^3$) and having a pH in the range of from about 4.5 to approximately 7.5 and
      said gel comprising a copolymer of potassium propenoate-propenamide pulverized to pass through a 20 mesh (0.0084 cm) screen;
   a membrane spanning the mouth of said cavity and being secured to said tray; and
   an aperture piercing said membrane at approximately the central portion of said mouth to receive a propagule therethrough, said aperture engaging said propagule physically to support said propagule and to maintain said propagule in a predetermined relationship with respect to the medium within said cavity.

2. A tissue culture assembly, as set forth in claim 1, in which the cavity wall is perforated to permit ingress and egress of fluids.

3. A tissue culture assembly, as set forth in claim 2, in which a plurality of cavities are suspended from a common web sheet.

4. A tissue culture assembly, as set forth in claim 3, in which the membrane is attached to the web sheet.

5. A tissue culture assembly, as set forth in claim 1, in which the amount of gel in said foam filler comprises from about 3 to 10 percent of the total medium by weight.

6. A tissue culture assembly, as set forth in claim 1, in which the cavity wall is perforated to permit ingress and egress of fluids.

7. A tissue culture assembly, as set forth in claim 6, in which a plurality of cavities are suspended from a common web sheet.

8. A tissue culture assembly, as set forth in claim 7, in which the membrane is attached to the web sheet.

* * * * *